United States Patent [19]
Raines et al.

[11] Patent Number: 5,252,044
[45] Date of Patent: Oct. 12, 1993

[54] PARENTERAL FLUID PUMP WITH DISPOSABLE CASSETTE

[75] Inventors: Aaron T. Raines; Raymond Santo, both of Dallas, Tex.

[73] Assignee: Medflow, Inc., Dallas, Tex.

[21] Appl. No.: 963,636

[22] Filed: Oct. 20, 1992

[51] Int. Cl.$^5$ .............................................. F04B 43/08
[52] U.S. Cl. ...................................... 417/479; 417/510
[58] Field of Search ............. 417/478, 479, 480, 510; 92/13.2

[56] References Cited

U.S. PATENT DOCUMENTS

| | | | |
|---|---|---|---|
| 3,982,534 | 9/1976 | Buckman | 128/214 C |
| 4,094,318 | 6/1978 | Burke et al. | 128/214 E |
| 4,155,362 | 5/1979 | Jess | 128/214 F |
| 4,168,288 | 9/1979 | Nau et al. | 417/479 X |
| 4,191,183 | 3/1980 | Mendelson | 128/214 R |
| 4,199,307 | 4/1980 | Jassawalla | 417/474 |
| 4,236,880 | 12/1980 | Archibald | 417/478 |
| 4,265,240 | 5/1981 | Jenkins | 128/214 E |
| 4,276,004 | 6/1981 | Hahn | 417/479 |
| 4,322,201 | 3/1982 | Archibald | 417/279 |
| 4,382,753 | 3/1983 | Archibald | 417/479 |
| 4,391,598 | 7/1983 | Thompson | 604/65 |
| 4,464,172 | 8/1984 | Lichtenstein | 605/65 |
| 4,468,222 | 8/1984 | Lundquist | 604/153 |
| 4,553,958 | 11/1985 | LeCocq | 604/67 |
| 4,657,490 | 4/1987 | Abbott | 417/478 |
| 4,696,671 | 9/1987 | Epstein et al. | 604/67 |
| 4,705,506 | 11/1987 | Archibald | 604/81 |
| 4,753,270 | 6/1988 | Lawhite et al. | 137/624 |
| 4,828,545 | 5/1989 | Epstein et al. | 604/66 |
| 4,865,584 | 9/1989 | Epstein et al. | 604/67 |
| 5,100,380 | 3/1992 | Epstein et al. | 604/67 |
| 5,108,367 | 4/1992 | Epstein et al. | 604/67 |

FOREIGN PATENT DOCUMENTS 9119098 12/1991 World Int. Prop. O. .......... 417/479

*Primary Examiner*—Richard E. Gluck
*Attorney, Agent, or Firm*—Ross, Howison, Clapp & Korn

[57] ABSTRACT

An ambulatory parenteral fluid infusion pump employs a disposable in-line cassette which provides three independent fluid paths between two flexible plastic sheets. The fluid path extends through a pump chamber having a piston plate secured to the flexible sheet at each pumping chamber. The sealed flexible sheets are housed in a rigid housing which provides an aperture through which a catch member formed on the piston plate extends, and having living hinges overlying the inlet and outlet paths for shutting off those paths. An outlet valve is normally closed, and operates in response to buildup of fluid pressure from advancement of the piston plate into the pump chamber to deliver fluid.

23 Claims, 6 Drawing Sheets

PARENTERAL FLUID PUMP WITH DISPOSABLE CASSETTE

TECHNICAL FIELD OF THE INVENTION

This invention relates to parenteral infusion pumps, and more particularly to an ambulatory pump with disposable in-line cassette suitable for independently controlled infusion of three fluids.

BACKGROUND OF THE INVENTION

The provision of instrumentation for the accurate infusion of intravenous fluids to patients has received substantial attention over the past two decades. Devices for providing controlled gravity flow, as well as flow induced by mechanical pressure, have been provided which consist of two major elements. The first is an instrument which the clinician programs with desired flow parameters and which contains electromechanical elements for controlling and monitoring flow. Such instruments ordinarily cooperate with an intravenous tubing set having a sealed fluid path which does not come in contact with the instrument. Typically included in the tubing set is an in-line cassette or other flow element which is positioned in the instrument during use.

The present invention provides a compact pump instrument suitable for wearing by an ambulatory patient, operating with a disposable in-line cassette providing the necessary valving and pumping functions for the infusion of three different fluids along independent flow paths. A device constructed in accordance with the invention is relatively simple and inexpensive, and employs a valving system which is not dependent upon the accuracy of alignment of the disposable cassette in the pump instrument. Despite the compactness of the pump instrument and the small size and simplicity of the disposable cassette, the system constructed in accordance with this invention permits the clinician to input independent flow rates and other flow parameters for three distinct fluids which are pumped along isolated flow paths to the output of the system. The fluids may be pumped simultaneously or sequentially, and the fluid output may be conveyed separately to distinct patient infusion sites, or combined in a single patient line as desired.

The pumping instrument of the invention utilizes a single drive motor for each fluid independently operated to actuate all of the essential pumping and valving actions necessary for accurate volumetric infusion of that fluid. In addition, a single drive is provided to actuate fail-safe shut down valving means of all fluid paths through the system.

SUMMARY OF THE INVENTION

In accordance with the invention, there is provided a disposable pump chamber cassette including a flexible diaphragm defining a chamber having an inlet and an outlet. A piston plate is secured to the flexible diaphragm adjacent the pump chamber and includes a upstanding catch. The cassette cooperates with an instrument which receives the cassette and incorporates drive means engaging the piston plate catch and moving the piston plate back and forth to draw fluid into, and expel fluid from, the pump chamber. Inlet valve closure means are carried by the instrument for closing the inlet of the pump chamber at selected times. A pressure responsive normally-closing outlet valve means is carried by the instrument for closing the outlet of the pump chamber except when the chamber is driven to an elevated pressure by the drive means, during which time it automatically opens.

In the specific embodiment disclosed, the cassette includes an array of three sets of pump chambers, piston plates, valves, and inlets and outlets, and the instrument includes pumping and valve means to independently drive the three portions of the cassette for independent and isolated delivery of three fluids.

In a specific embodiment of the invention, the pressure responsive outlet valve is monitored by sensing means to determine the position of the outlet valve. In a further aspect of the invention, fail-safe shutoff means is provided for closing the outlet of all chambers of the cassette.

In a specific form of the invention, the cassette includes two flexible plastic sheets welded together to form three fluid paths, each extending from an inlet to an outlet extending through a pumping chamber positioned between the sheets. One wall of the pumping chamber may be formed by a rigid cup shaped member adhered to one of the flexible sheets at an aperture therein.

In a preferred embodiment of the invention, each fluid path extends from an inlet to an outlet provided side by side on the edge of the cassette so as to be accessible when the cassette is installed in the instrument.

BRIEF DESCRIPTION OF THE DRAWINGS

For a more complete understanding of the present invention and for further advantages thereof, reference is now made to the following Description of the Preferred Embodiment taken in conjunction with the accompanying Drawings in which.

DESCRIPTION OF THE PREFERRED EMBODIMENTS

Figure 3:
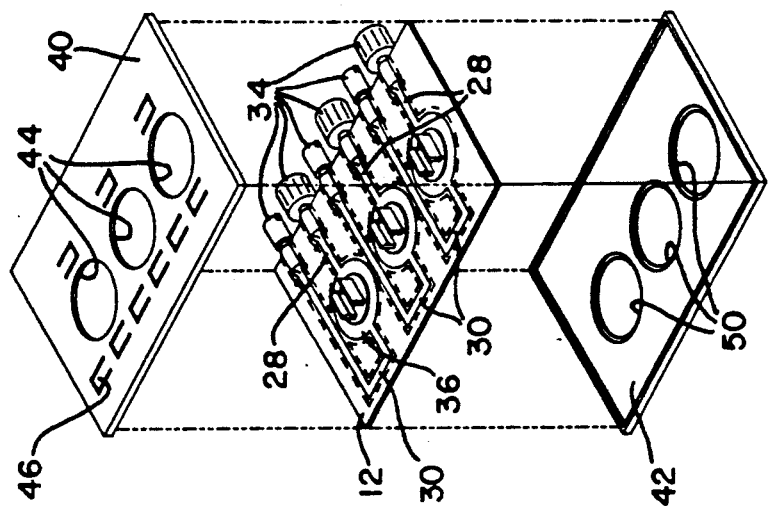
FIGS. 1–3 are schematic illustrations of the construction of a disposable pump cassette in accordance with the invention.
Figure 2:
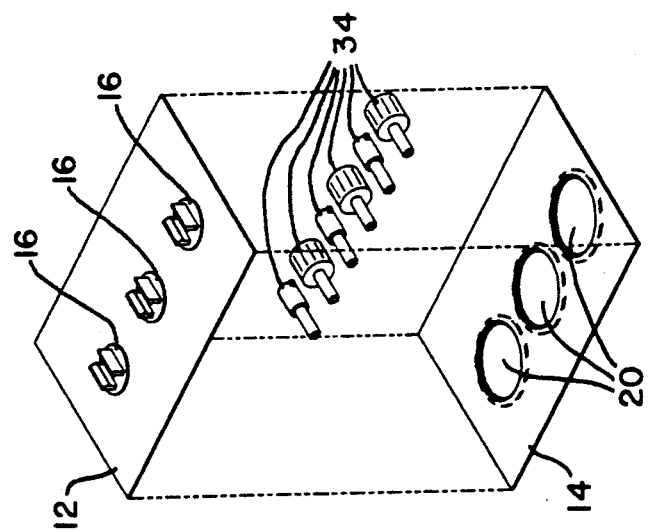
Figure 1:
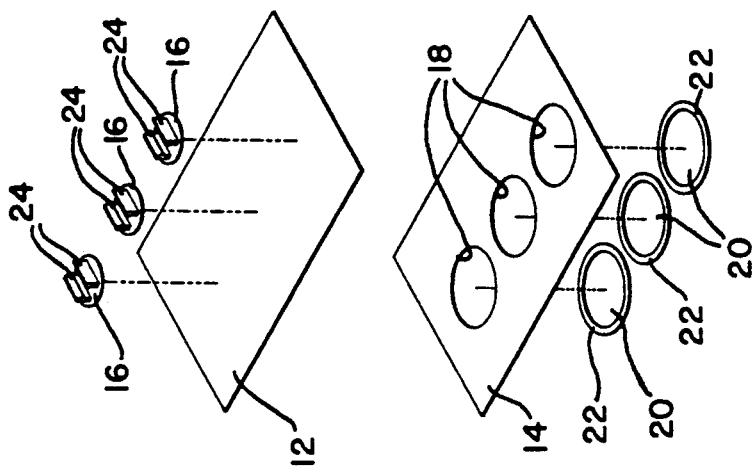

The construction of a cassette 10 for an ambulatory parenteral pump providing pumping of three separate infusates is depicted in FIGS. 1 through 3. Three fluid paths in the cassette are provided between an upper flexible plastic sheet 12 and a lower flexible plastic sheet 14. Sheets 12 and 14 may be formed from any suitable flexible plastic material such as polyvinylchloride. Upper sheet 12 is provided with three spaced pump piston plates 16 on its upper surface. Lower flexible sheet 14 has three spaced die-cut apertures 18 in register with piston plates 16. Three rigid cup shaped members 20 are positioned beneath lower sheet 14 in surrounding relationship to apertures 18. Securement of rigid cups 20 underlying apertures 18 may be affected by radio frequency welding of cup surrounding flanges 22 to the underside of flexible sheet 14. Likewise, piston plates 16 may be secured to the upper flexible sheet by radio frequency welding. Each piston plate 16 has integrally formed therewith a pair of opposed upstanding catch members 24 which protrude upwardly from piston plate 16 away from flexible sheet 12.

Sheets 12 and 14 may be secured together in a single step by radio frequency welding. The sealing includes definition of an inlet fluid path 28 corresponding to each rigid cup shaped member 20 and an outlet fluid path 30 leading from each rigid cup shaped member 20. The inlet path 28 and outlet path 30 corresponding to each cup shaped member 20 are arranged so that they terminate at the same edge 32 of bonded sheets 12 and 14 in side-by-side relationship. Each inlet and outlet is provided with a Luer fitting 34 of conventional configuration for connection to upstream and downstream tubing connecting the cassette to, respectively, a fluid source and a patient. Sheets 12 and 14 are sealed about the periphery of aperture 18 so as to form a pumping chamber 36 with each cup shaped member 20. Thus, flexible sheets 12 and 14 define a series of three sealed independent flow paths, each extending from an inlet 28 with fitting 34, through a pump chamber 36, to an outlet 38 with fitting 34.

Figure 5:
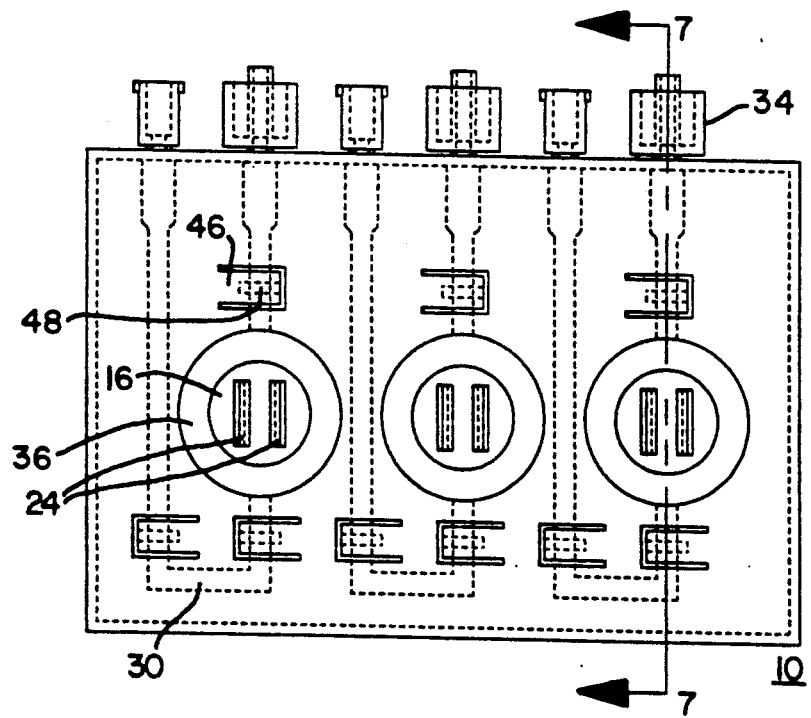
FIG. 5 is a plan view of the cassette of FIG. 4.

The sealed flexible sheets 12 and 14 are then secured between upper rigid housing member 40 and lower rigid housing member 42 by means of sonic welding around the periphery of the cassette, capturing the flexible diaphragm sheets 12 and 14 and their sealed flow paths in fixed geometric relationship to the housing members 40 and 42. Upper rigid housing member 40 is provided with three apertures 44 each surrounding pump chamber 36 and permitting upstanding catch members 24 to extend upwardly through upper housing member 40. The surface of upper housing member 40 is also provided with nine living hinge members formed therein, and designated by the reference numeral 46. One of the living hinge members 46 overlies the inlet channel 28 of each fluid flow path. Two of the living hinge members 46 are provided at spaced locations along each outlet channel 30. As seen in FIG. 5, in phantom, the lower portion of each living hinge member 46 is provided with downwardly extending protrusion 48 which will act, upon application of force to its living hinge 46, to shut off the underlying flow channel formed between flexible sheets 12 and 14.

Figure 4:
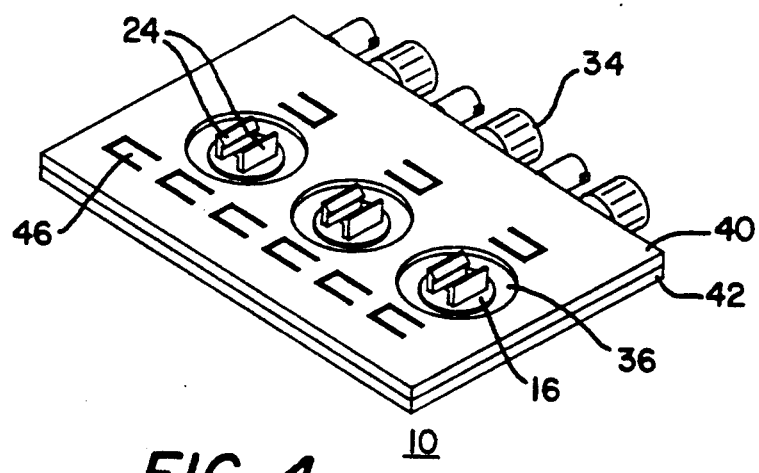
FIG. 4 is a perspective view of the disposable pump cassette constructed in accordance with the invention.

Lower rigid housing member 42 is provided with an aperture 50 for receiving each of the rigid cup members 20 of flexible sheet 14. The assembled cassette, as seen in FIGS. 4 and 5, thus provides fluid inlet and outlet connections for three isolated fluid paths, each of which extends through a pump chamber. The rigid housing provides access to catch means 24 for exercising the pump chamber. Living hinges 46 provide the capability of shutting off the inlet channel and the outlet channel, the latter at two spaced locations. The pump cassette provides, in one compact and inexpensive package, three essentially identical isolated fluid paths for controlling infusions of three infusates. Infusion may proceed, by the clinician's selection of downstream tubing configurations, into separate patient sites or into a single delivery cannula.

Figure 6:
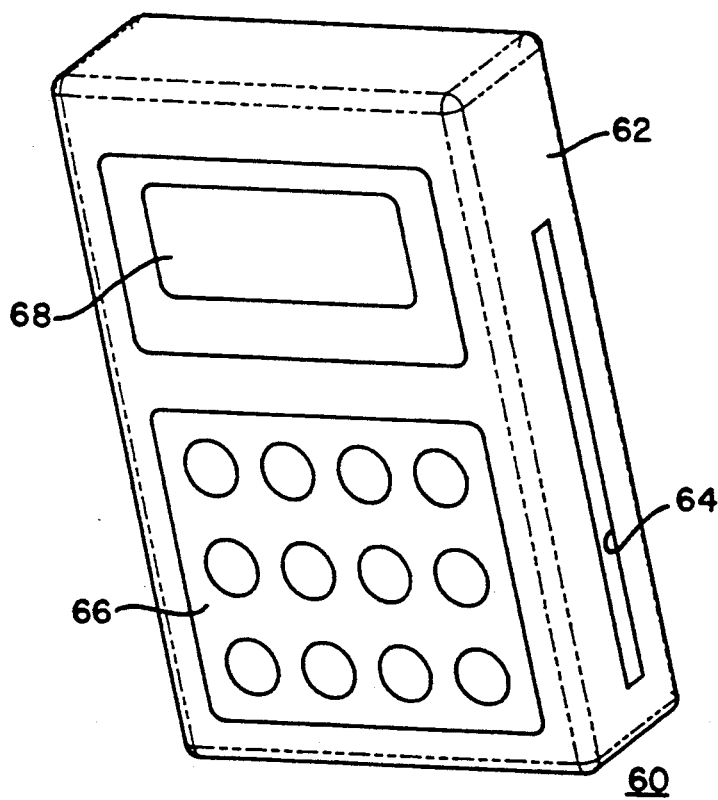
FIG. 6 is a perspective view of an ambulatory pump instrument for use with the cassette of FIG. 1.

FIG. 6 illustrates a compact ambulatory pump instrument 60 for receiving and exercising the pumping cassette 10. Instrument 60 has a case 62 with a cassette receiving slot 64 formed in its side. A conventional keyboard 66 is provided for inputting infusion instructions for each of the three independent fluid paths. A conventional display 68 is provided for displaying alpha/numeric information for setup instructions, input data and information concerning infusions in progress. Instrument 60 is powered conventionally using a battery. As conventional, the instrument may also be powered by AC connection as, for example, when the patient has retired to bed or other fixed location.

Figure 7:
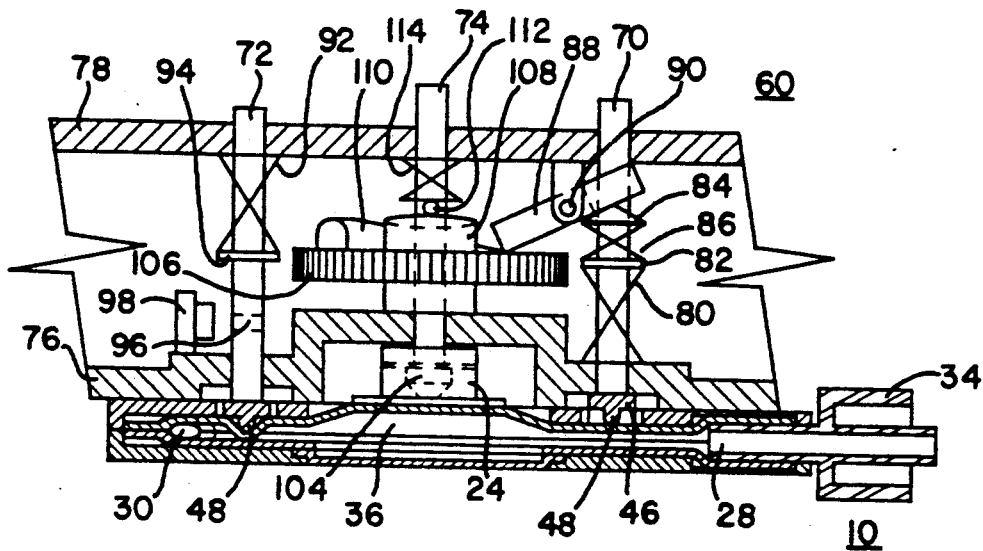
FIG. 7 is a schematic cross-section, along line 7—7 of FIG. 5, illustrating the cooperation of the cassette with the drive means of the instrument, with the pump chamber shown in the full position, ready to pump.
Figure 8:
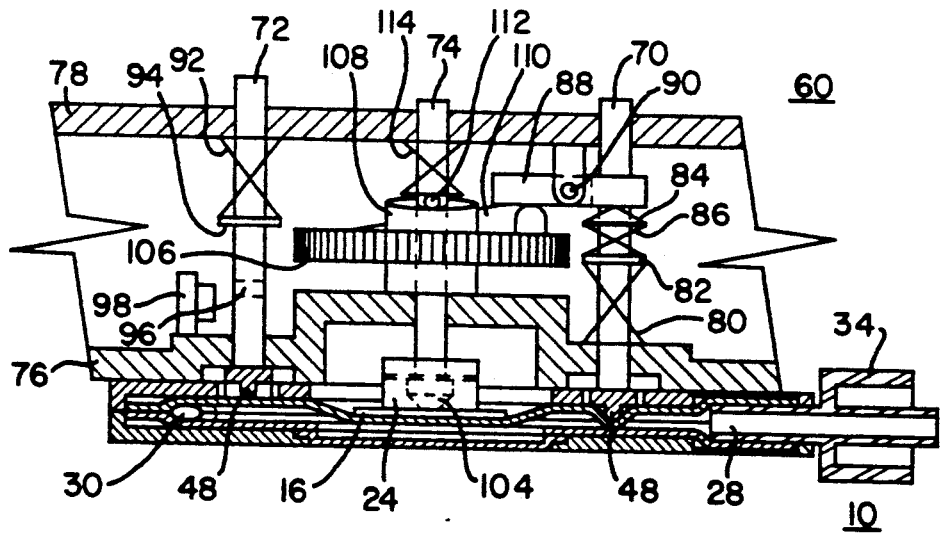
FIG. 8 is a view similar to FIG. 7, with the pump chamber emptying during a pumping stroke.

The pumping and valving operations on each of the cassette fluid paths are provided in instrument 60 by three identical mechanisms, a single one of which is shown in operating position with cassette 10 in FIGS. 7 and 8. The mechanism includes inlet valve shaft 70, outlet valve shaft 72, and pumping shaft 74, each carried slidingly by apertures in front bezel 76 and spaced rear mounting plate 78. Cassette 10 is held firmly against front bezel 76 in operating position by a conventional holding mechanism (not shown). In this position, inlet valve shaft 70 directly confronts and engages the living hinge 46 overlying the inlet fluid channel 28 for one fluid. Shaft 70 is biased to the retracted or open position by spring 80 mounted about shaft 70 between front bezel 76 and shoulder 82 carried fixedly by shaft 70. A force receiving member 84 is mounted around shaft 70 so that it may float up and down with respect to the shaft on overriding spring 86. The lower end of spring 86 is mounted on shoulder 82. Shaft 70 may be extended toward cassette 10 to cause the living hinge projection 48 to close inlet channel 28 by application of force on member 84 through lever 88 pivoted at fulcrum 90, as shown in FIG. 8.

Outlet valve shaft 72 is not operated directly by the instrument 60, but is biased to the closing position by spring 92 bearing on shoulder 94 to cause living hinge 46 overlying inlet channel 30 to close the channel. The valve is thus normally closed, but responsive to fluid pressure in the pump chamber 36 to open and permit flow outwardly along outlet channel 30 from pumping chamber 36. Outlet valve shaft 72 includes a magnetically permeable portion 96 for tracking the position of shaft 72. Hall effect sensor 98 is mounted to the front bezel 76 adjacent magnetic portion 96 to detect the position of the valve.

Pumping shaft 74 includes a drive head 104 which is captured by the upstanding catch members 24 so that it is held tightly against piston plate 16. By this engagement, reciprocal movement of the drive shaft 74 will cause piston plate 16 to be moved toward and away from the cup shaped member 20 defining the pump chamber 36 in cassette 10. Actuation of inlet valve shaft 70 and pump drive shaft 74 is effected by unidirectional driving of camming gear 106 which rotates about shaft 74. The upper surface of gear 106 carries outer inlet valve camming surface 108 and inner pump camming surface 110. Gear 106 is driven by a drive gear 107 (FIG. 9) carried in instrument 60, which is rotated by an electric motor (not shown). Inlet valve camming surface 108 causes the lever 88 to advance and retract inlet valve shaft 70. Piston shaft 74 carries a camming pin 112 which is kept in contact with camming surface 110 by spring 114.

Figure 9:
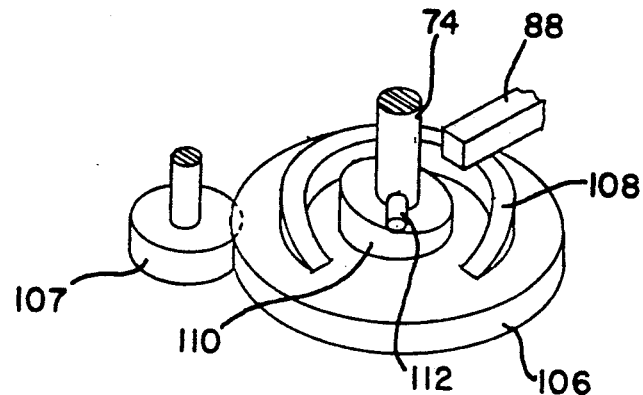
FIG. 9 is a schematic illustration of the instrument drive means camming system for the pumping chamber and inlet valve.
Figure 10:
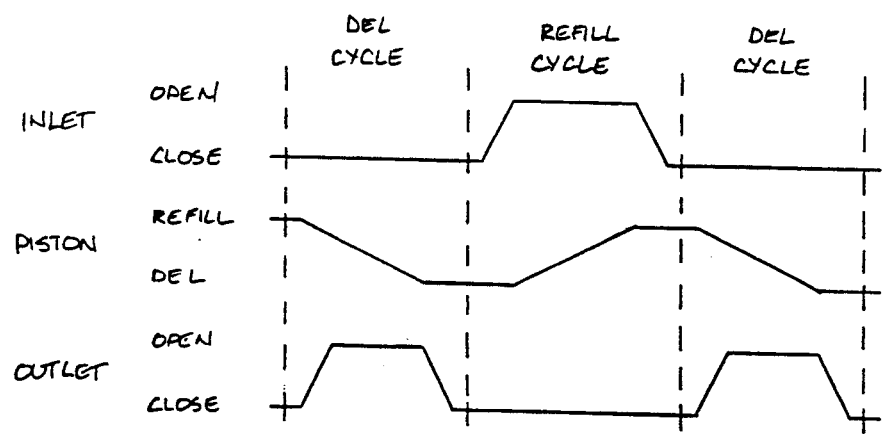
FIG. 10 is a timing diagram illustrating a pump cycle.

This camming action is schematically illustrated in FIG. 9. FIG. 10 illustrates the cycle of movement of valve shaft 70 and pumping shaft 74 under the control, of camming gear 106. The lower curve in FIG. 10 illustrates the pressure response of the passive outlet valve of shaft 72. At the start of the time period depicted in FIG. 10, inlet shaft 70 is held in the closed position, occluding channel 28. Piston plate 16 is in the retracted or refill position, indicating a full load in pumping chamber 36. Pumping begins initially by causing the pumping shaft 74 to advance propelling the plate 16 toward pumping chamber 36. As pressure builds in pumping chamber 36, outlet valve shaft 72 opens to permit flow outwardly through outlet channel 30. This condition is maintained until pumping shaft 74 completes its downward travel with the piston plate 16 ceasing to pressurize chamber 36. The opening and closing of outlet valve shaft 72 is sensed by sensor 98 so that the instrument has verification of the amount of movement of pumping shaft 74, and thus piston plate 16 during the time outlet channel 30 is open. After closing of the outlet channel 30, the inlet valve shaft 70 is moved to the open position, and the piston shaft 74 subsequently retracted, pulling fluid into chamber 36 through inlet 28 as piston plate 16 moves toward its initial retracted position. Then inlet valve shaft 70 is advanced to close channel 28, and the cycle begins again.

It will be appreciated that the foregoing arrangement has a number of advantages. The precise cycling of inlet valve and pump is controlled by a single camming gear 106 which is driven in a single direction. The fabrication of the cassette 10 aligns the living hinges 56 and inlet and outlet channels 28 and 30 so that accurate closure capability is established in the fabrication process for cassette 10, and not through the alignment of individual disposable cassettes 10 in the instrument 60.

Figure 11:
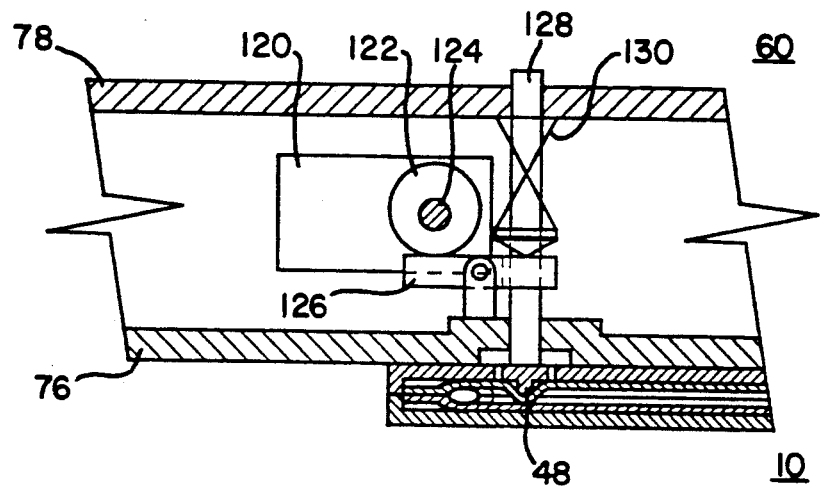
FIG. 11 is a schematic cross-sectional view illustrating a fail-safe shut down valve on the instrument, with the valve closed.
Figure 12:
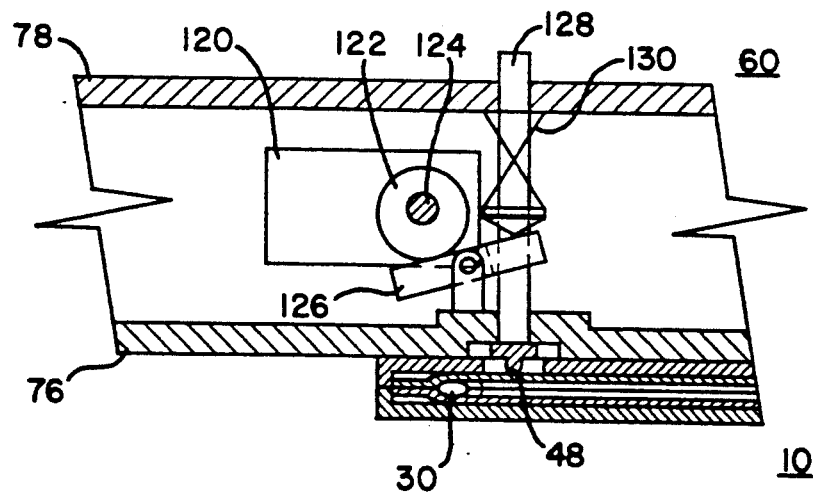
FIG. 12 is a view similar to FIG. 11, with the fail-safe valve open.

In FIGS. 11 and 12, there is depicted a fail-safe closure valve for operation on the most downstream living hinge 48 for each fluid path. By a single motor operating through three cams, one for each of the three fluid paths, all fluid paths of the cassette may be placed in the no-flow condition in response to any selected alarm messages. For example, if the outlet valve sensor 98 fails to detect proper movement of outlet valve shaft 72 in response to the pumping cycle, a message can be sent to the system for shutdown of all three fluid paths. A shutdown motor 120 drives three cams 122 mounted on gear shaft 124. The cams are operable between a first closed position depicted in FIG. 11 and a second open position depicted in FIG. 12. Through lever 126, each cam 122 operates to position fail-safe valve shaft 128, which is biased by spring 130 to the closed position depicted in FIG. 11.

Whereas the present invention has been described with respect to a specific embodiment thereof, it will be understood that various changes and modifications will be suggested to one skilled in the art and it is intended to encompass such changes and modifications as fall within the scope of the appended claims.

We claim:
1. A parenteral fluid pump comprising:
   (a) a disposable pump chamber cassette including a flexible diaphragm defining a chamber having an inlet and an outlet;
   (b) a piston plate welded to the flexible diaphragm of the pump chamber, including an upstanding catch;
   (c) an instrument for receiving the disposable cassette in an operating position;
   (d) drive means carried by the instrument including means for engaging the piston plate catch and moving the piston plate back and forth to draw fluid into, and expel fluid from the pump chamber;
   (e) inlet valve closure means carried by the instrument for closing the inlet of the pump chamber at selected times;
   (f) pressure responsive normally-closing outlet valve means carried by the instrument for closing the outlet of the pump chamber except when the chamber is driven to an elevated pressure by the drive means.

2. The pump of claim 1, wherein the cassette includes two additional sets of pump chambers, piston plates, inlet and outlets, and the instrument includes two additional sets of drive and valve means for independent and isolated delivery of two additional infusates.

3. The pump of claim 1, further comprising sensing means for sensing the position of the outlet valve means.

4. The pump of claim 1, further comprising fail-safe shut-off means for closing the outlet of the chamber.

5. The pump of claim 4, wherein the shut-off means responds at least to the sensing means.

6. The pump of claim 1, wherein the cassette includes a rigid housing encompassing the pump chamber having an aperture through which the piston plate catch extends, and a living hinge overlying the pump chamber inlet for engagement by the inlet valve closure means, and a living hinge overlying the pump chamber outlet for engagement by the outlet valve means.

7. A disposable cassette for an intravenous pump comprising:
   a. a first flexible plastic sheet;
   b. a second flexible plastic sheet having an aperture formed therein and having a rigid cup-shaped member adhered thereto about the aperture to form a pumping chamber wall; said second flexible sheet being selectively welded to the first flexible sheet to form an inlet channel leading from an edge of the cassette to the cup-shaped member, an outlet channel leading from the cup-shaped member to an edge of the cassette, and a generally circular seal around the cup-shaped member to form the pumping chamber;
   c. a flat pumping plate secured to the first flexible sheet opposite the cup-shaped member, and having an upstanding catch;
   d. a rigid housing enclosing the first and second flexible plastic sheets and having an aperture through, which the catch extends, and having a first living hinge formed on its surface overlying the inlet channel, and a second living hinge formed on its surface overlying the outlet channel; and
   e. fittings secured at the edge of the rigid housing communicating with the inlet and outlet channels, so that a fluid circuit is formed extending between said fittings through a pump chamber formed by the cup-shaped member and the first flexible sheet, whereby the pump chamber may be activated by mechanical interface with the catch, and the inlet and outlet channels may be closed at selected times by external pressure on the living hinges of the rigid housing.

8. The cassette of claim 7, wherein the pumping plate is circular, and the catch comprises a pair of spaced arms upstanding from the plate with confronting detent shoulders formed on the arms.

9. The cassette of claim 7, wherein the cup-shaped member includes a surrounding flange which is seamed to the second flexible sheet.

10. A disposable cassette for an intravenous pump comprising:
  a. a first flexible plastic sheet;
  b. a second flexible plastic sheet having three spaced apertures formed therein and having three rigid cup-shaped members adhered thereto about the apertures, each forming a wall of a pumping chamber; said second flexible sheet being selectively welded to the first flexible sheet to form an inlet channel leading from an edge of the cassette to each cup-shaped member, an outlet channel leading from each cup-shaped member to an edge of the cassette, and a generally circular seal around each cup-shaped member to form said pumping chamber;
  c. a rigid catch secured to the first flexible sheet opposite each cup-shaped member;
  d. a rigid housing enclosing the first and second flexible plastic sheets and having an aperture through which each catch extends, and having a first living hinge formed on its surface overlying each inlet channel, and a second living hinge formed on its surface overlying each outlet channel; and
  e. fittings secured at the edge of the rigid housing communicating with the inlet and outlet channels so that three isolated and independent fluid circuits are formed, each extending between a pair of fittings through a pumping chamber formed by one of said cup shaped members and the first flexible sheet, whereby each pumping chamber may be activated independently by mechanical interface with its catch, and each inlet and outlet channel may be closed at selected times by external pressure on the living hinges of the rigid housing.

11. The cassette of claim 10, wherein the catch comprises a pair of upstanding spaced arms with confronting detent shoulders formed on the arms.

12. The cassette of claim 10, wherein the cup-shaped member includes a surrounding flange which is secured to the second flexible sheet.

13. A disposable cassette for an intravenous pump comprising:
  a. a first flexible plastic sheet;
  b. a second flexible plastic sheet selectively welded to the first flexible sheet to form a pumping chamber, an inlet channel leading from an edge of the cassette to the pumping chamber and an outlet channel leading from the pumping chamber to an edge of the cassette;
  c. a flat pumping plate secured to the first flexible sheet adjacent the pumping chamber;
  d. an upstanding catch formed on the pumping plate opposite the first flexible sheet; and
  e. fittings secured at an edge of the cassette communicating with the inlet and outlet channels so that a fluid circuit is formed extending between said fittings through the pumping chamber.

14. The cassette of claim 13, wherein the catch comprises a pair of spaced arms formed with opposed detent shoulders.

15. A disposable cassette for an intravenous pump comprising:
  a. a first flexible plastic sheet;
  b. a second flexible plastic sheet having an aperture former therein and having a rigid cup-shaped member adhered about the aperture to form a pumping chamber, said second flexible sheet being selectively welded to the first flexible sheet to form an inlet channel leading from an edge of the cassette to the cup-shaped member, an outlet channel leading from the cup-shaped member to an edge of the cassette, and a circular seal around the cup-shaped member to form the pumping chamber;
  c. a flat pumping plate, secured to the first flexible sheet opposite the cup-shaped member;
  d. a catch formed on the plate opposite the first flexible sheet; and
  e. fittings secured at an edge of the cassette communicating with the inlet and outlet channels so that a fluid circuit is formed extending between said fittings through a pumping chamber formed in the cassette between the cup-shaped member and the first flexible sheet.

16. The cassette of claim 15, wherein the cup-shaped member includes a surrounding flange which is bonded to the second flexible sheet.

17. A disposable cassette for an intravenous pump comprising:
  a. a first flexible plastic sheet;
  b. a second flexible plastic sheet having an aperture formed therein and having a rigid cup-shaped member adhered thereto to form a wall of a pumping chamber; said second flexible sheet being selectively welded to the first flexible sheet to form an inlet channel leading from an edge of the cassette to each cup-shaped member, an outlet channel leading from each cup-shaped member to an edge of the cassette, and a circular seal around each cup-shaped member to form a pumping chamber;
  c. a rigid catch secured to the first flexible sheet opposite each cup-shaped member; and
  d. a rigid housing enclosing the first and second flexible plastic sheets and having an aperture through which the rigid catch extends.

18. The cassette of claim 17, wherein the catch comprises a pair of upstanding spaced arms with confronting detent shoulders formed on the arms.

19. The cassette of claim 17, wherein the cup-shaped member includes a surrounding flange which is secured to the second flexible sheet.

20. A disposable cassette for an intravenous pump comprising a pair of flexible plastic sheets selectively welded together to form:
  a. a first pumping chamber;
  b. a first inlet channel leading from an edge of the cassette to the first pumping chamber having a first inlet valve site;
  c. a first outlet channel leading from the first pumping chamber to an edge of the cassette having a first outlet valve site;
  d. a second pumping chamber;
  e. a second inlet channel leading from an edge of the cassette to the second pumping chamber having a second inlet valve site;
  f. a second outlet channel leading from the second pumping chamber to an edge of the cassette having a second outlet valve site;
  g. a third pumping chamber;

h. a third inlet channel leading from an edge of the cassette to the third pumping chamber having a third inlet valve site; and
i. a third outlet channel leading from the third pumping chamber to an edge of the cassette having a third outlet valve site, whereby three fluids may be pumped through the cassette along three isolated and independent paths.

21. The cassette of claim 20, further comprising a rigid housing enclosing the flexible sheets.

22. The cassette of claim 21, further comprising living hinges formed on one surface of the rigid housing, one overlying each valve site.

23. A disposable cassette for an intravenous pump comprising:
a. a first flexible plastic sheet;
b. a second flexible plastic sheet selectively welded to the first flexible sheet to form a pumping chamber, an inlet channel leading from an edge of the cassette to the pumping chamber, an outlet channel leading from the pumping chamber to an edge of the cassette; a seal around the cup-shaped member to form said pumping chamber;
c. a catch secured to the first flexible sheet opposite the cup-shaped member; and
d. a rigid housing enclosing the first and second flexible plastic sheets and having an aperture through which the catch extends, and having a first living hinge formed on its surface overlying the inlet channel, and a second living hinge formed on its surface overlying the outlet channel.

* * * * *